United States Patent
Gray, Jr. et al.

[11] Patent Number: 6,149,687
[45] Date of Patent: Nov. 21, 2000

[54] OFFSET TRIAL STEM

[75] Inventors: Wayne P. Gray, Jr., Pflugerville, Tex.; Dennis L. Armstrong, Mesa, Ariz.

[73] Assignee: Sulzer Orthopedics Inc., Austin, Tex.

[21] Appl. No.: 09/113,787

[22] Filed: Jul. 10, 1998

[51] Int. Cl.[7] .................................................. A61F 2/38
[52] U.S. Cl. .................................. 623/20.34; 623/20.32; 623/23.47
[58] Field of Search ................................ 623/18, 20, 22, 623/23, 20.14, 20.15, 20.32–20.34, 23.47

[56] References Cited

U.S. PATENT DOCUMENTS

| | | | |
|---|---|---|---|
| 4,106,128 | 8/1978 | Greenwald et al. | 623/20 |
| 4,268,920 | 5/1981 | Engelbrecht et al. | 623/18 |
| 4,676,797 | 6/1987 | Anapliotis et al. | 623/23 |
| 5,133,760 | 7/1992 | Petersen et al. | 623/20 |
| 5,271,737 | 12/1993 | Baldwin et al. | 623/20 |
| 5,290,313 | 3/1994 | Heldreth | 623/20 |
| 5,593,449 | 1/1997 | Roberson, Jr. | 623/18 |
| 5,601,567 | 2/1997 | Swajger et al. | 606/86 |
| 5,702,480 | 12/1997 | Kropf et al. | 623/23 |
| 5,782,920 | 7/1998 | Colleran | 623/18 |
| 5,944,756 | 8/1999 | Fischetti et al. | 623/18 |

Primary Examiner—V. Millia
Assistant Examiner—Tram A. Nguyen
Attorney, Agent, or Firm—Philip S. Lyren

[57] ABSTRACT

An offset trial stem system includes a baseplate and a trial stem. The trial stem has a main body portion and a baseplate connection portion. The baseplate connection portion is threadably attached to the baseplate, and is offset from, and connected to, the main body portion by a transition portion. A threaded member is provided for attaching the trial stem to the baseplate. The threaded member is mounted for reciprocating and rotating movement in the trial stem.

34 Claims, 3 Drawing Sheets

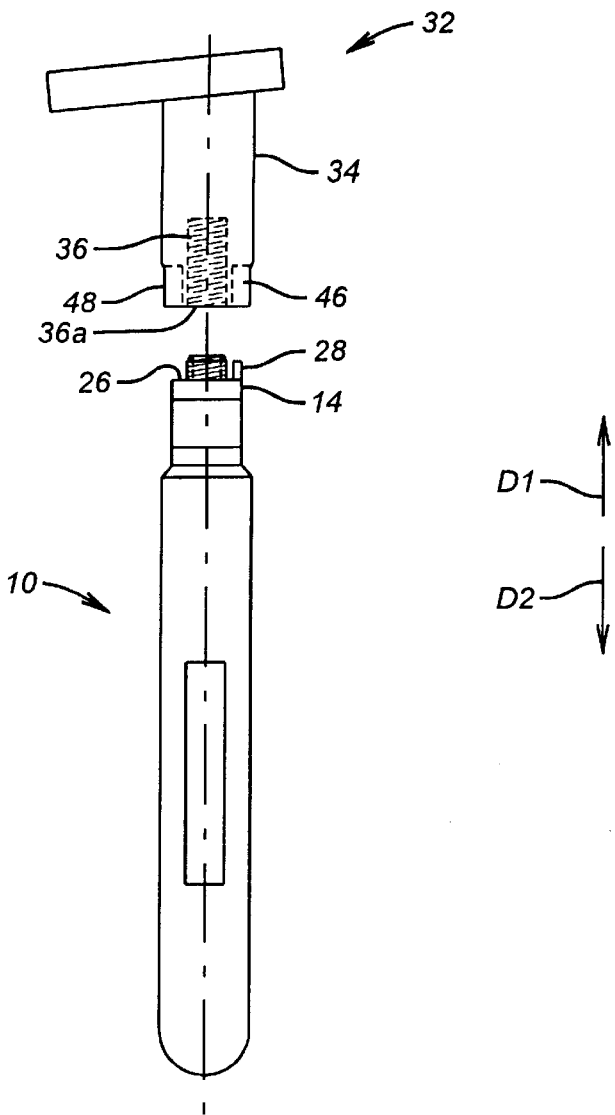
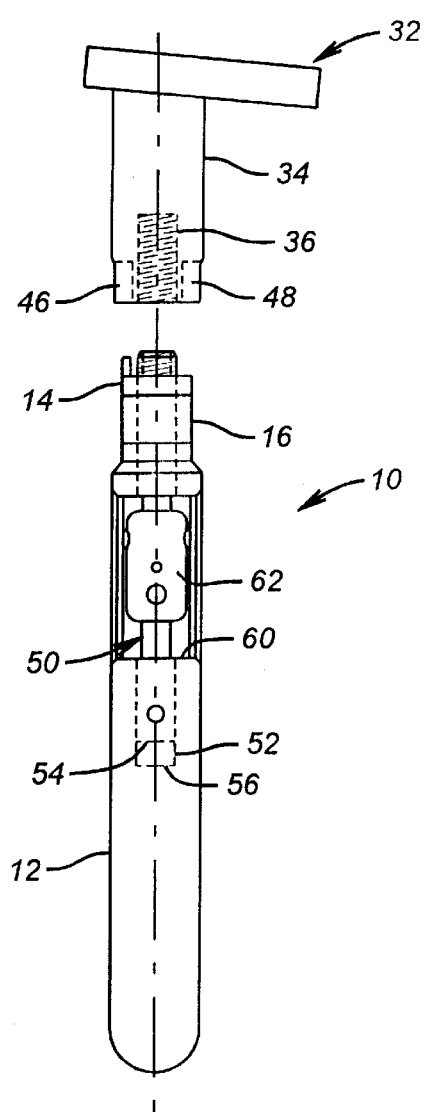
FIG. 2
FIG. 4
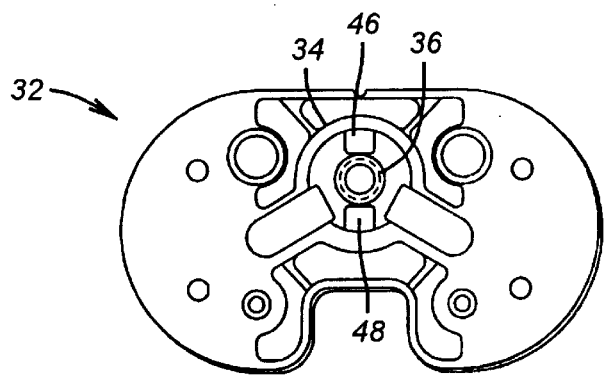
FIG. 3

OFFSET TRIAL STEM

BACKGROUND

The disclosures herein relate generally to knee implants and more particularly to a trial stem including an offset which can be used to locate the trial baseplate position medially or laterally.

Primary tibial implants often fail and must be replaced with a revision implant. An often encountered problem confronting a revision implant is bone loss and implant stability. The result of bone loss is that it precludes attaching a replacement implant directly to the proximal end of the tibia in the same manner as a primary implant by a fastening device or cement. Instead, the proximal end of the tibia is resected and a bore is formed using the intramedullary canal as a guide through the resected proximal end of the tibia to permit the placement of an implant stem. A baseplate is attached to the stem abutting the resected end of the tibia to receive and support an articulating surface.

The anatomy of the human tibia is variable. The tibia comprises an outer layer of hard cortical bone and an inner filling of relatively soft cancellous bone. The strength of the tibia is primarily derived from the cortical bone and should be preserved to support implants. Normally, the intermedullary canal is not in the actual center of the proximal tibia. As a result, when the bore is formed using the intramedullary canal, the stem which is placed in the bore may not be centered within the proximal tibia. Because the baseplate is mounted on the stem, the baseplate may not be ideally positioned with respect to the resected tibial surface. This can result in an overhang of the baseplate relative to the resected end of the tibia and a resulting irritation of soft surrounding tissue. The baseplate must therefore be kept within the confines of the tibia. As a result, it is often necessary to provide an offset, either medially or laterally, in order to properly orient the baseplate on the proximal tibia relative to the stem.

A surgeon may prefer to press-fit a tibial stem in the canal instead of cementing. In that case, the entire tibial canal is subsequently reamed out, i.e. all cancellous bone is removed. A good cortical fit is desired. Reaming is accomplished by using various sized reamers and progressively increasing the reamer size to reach the desired canal diameter and depth. Subsequently, the surgeon trials with various size straight tibial stems having a baseplate threadably attached, to find a stable press-fit with the cortical bone, but may find that the baseplate overhangs the proximal tibia. To correct for the overhang, the surgeon downsizes from the press-fit stem to a cemented stem in an effort to properly locate the baseplate, and then cements the implants in position.

If the bore is offset to compensate for the off-center canal within the tibia, the implant may be supported on some surface areas by the hard cortical bone and on other surface areas by the relatively softer cancellous bone. This is undesirable and may require a filler cement to stabilize and secure the stem. Also, if a subsequent replacement is required, the filler must be removed.

One attempt to overcome the above-mentioned problems with tibial stem implants is addressed in U.S. Pat. No. 5,133,760, which provides a universal modular prosthetic stem extension which may be installed on a prosthesis in a multiplicity of different orientations to compensate for a multiplicity of patient conditions. The stem includes a coupling mechanism allowing the stem to be rotated to any one of a multiplicity of rotative positions with respect to a prosthetic base so that the stem may be fixed in position relative to the base.

Another device is disclosed in U.S. Pat. No. 5,271,737 which comprises a combination baseplate fixed to an offset, straight tibial stem. The base includes an inferior surface for abutting a resected surface of the patient's tibia. The longitudinal center axis of the straight tibial stem extends from the inferior surface of the base and is offset from a center of the base. Interestingly, the offset places the stem in position to extend into the canal of the tibia so that it does not interfere with the cortical bone. As a result of the fixed arrangement, one baseplate and stem is required for a medial offset and another is required for a lateral offset.

A further device is disclosed in U.S. Pat. No. 5,290,313, which comprises a modular prosthesis system including a modular stem which has an attachment section for attachment to the base, a main body section for implanting into the canal in the tibia, and an angled transition section. The attachment section and main body section each include a respective longitudinal axis. These axes are parallel to each other and spaced apart to provide an offset therebetween. The offset is substantial, such that the axis of the attachment section intersects the transition section.

However, although offset stem implants are provided, accuracy requires a satisfactory trial stem and trial baseplate which simulate the offset of the stem and baseplate implants.

Therefore, what is needed is an offset trial stem which can be attached to a trial baseplate so that when the offset trial stem is attached to the trial baseplate and set into the canal, they are in the same orientation as the offset tibial stem and baseplate will be when implanted.

SUMMARY

One embodiment, accordingly, provides an offset, trial system that allows a surgeon to interoperatively center a trial stem and baseplate on the proximal tibia of the patient, which simulates the offset of the stem and baseplate implants. To this end, an offset trial stem comprises a main body portion, a baseplate connection portion, and a transition portion. The baseplate connection portion and the main body portion are interconnected by the transition portion which offsets the baseplate connection portion from the main body portion. A threaded member is provided for attaching the trial stem to the baseplate. The threaded member is mounted for rotating movement in the trial stem.

The principal advantage of this embodiment is that, interoperatively, a surgeon using a present trial baseplate which is used with a straight trial stem, can attach an offset trial stem, thus providing the same fit and orientation that will be provided when the actual offset stem and baseplate are implanted.

BRIEF DESCRIPTION OF THE DRAWINGS

FIG. 2 is a side view taken along line 2—2 of FIG. 1.

FIG. 3 is a view taken along line 3—3 of FIG. 1.

FIG. 4 is a view taken along line 4—4 of FIG. 1

DETAILED DESCRIPTION OF THE PREFERRED EMBODIMENT

Figure 1:
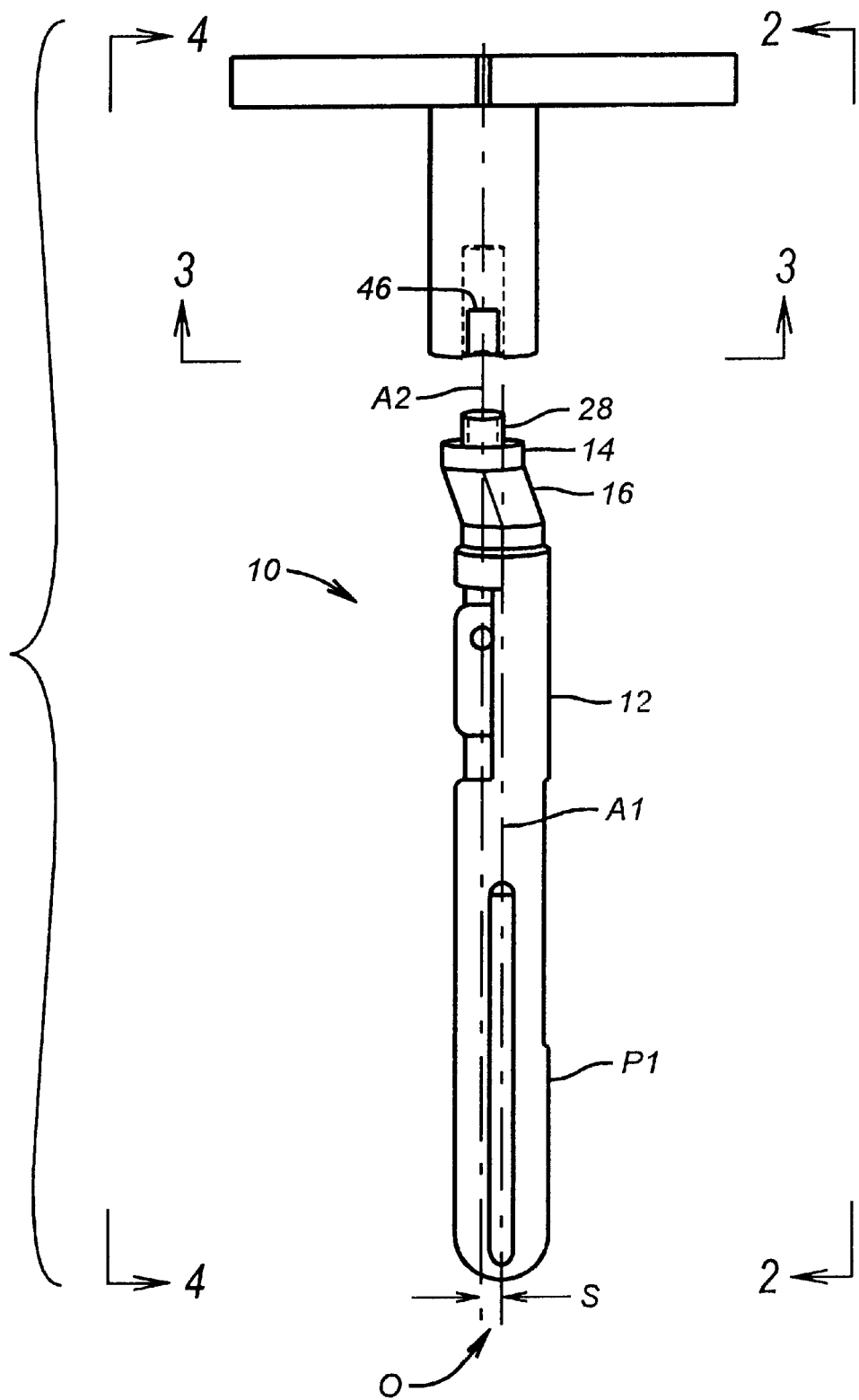
FIG. 1 is a frontal view illustrating an embodiment of a trial stem and trial baseplate.

An offset trial stem is illustrated in FIG. 1, and is designated 10. Stem 10 includes a main body portion 12 and a baseplate connection portion 14. The baseplate connection portion 14 is offset from and connected to the main body portion 12 by an intermediate transition portion 16 which is angularly disposed relative to portions 12 and 14, and functions to provide and offset, designated O, between the main body portion 12 and the baseplate connection portion 14.

The amount of offset O between main body portion 12 and the baseplate connection portion 14 is illustrated by a space, designated S, between a first centroidal axis designated A1 extending through the main body portion 12, and a second centroidal axis designated A2, substantially parallel to the first centroidal axis A1, and extending through the baseplate connection portion 14. The space S is of a dimension, i.e. about 3 mm, such that both the first centroidal axis A1, and the second centroidal axis A2, each pass through the main body portion 12. This dimension has been formed to provide a suitable offset for most required offsets to correct the tibial baseplate position either medially or laterally. Stem 10, FIG. 2, includes an end surface 26 on the baseplate connection portion 14 having a key member or tab 28 extending axially therefrom and situated on one side of the baseplate connection portion 14.

Figure 5:
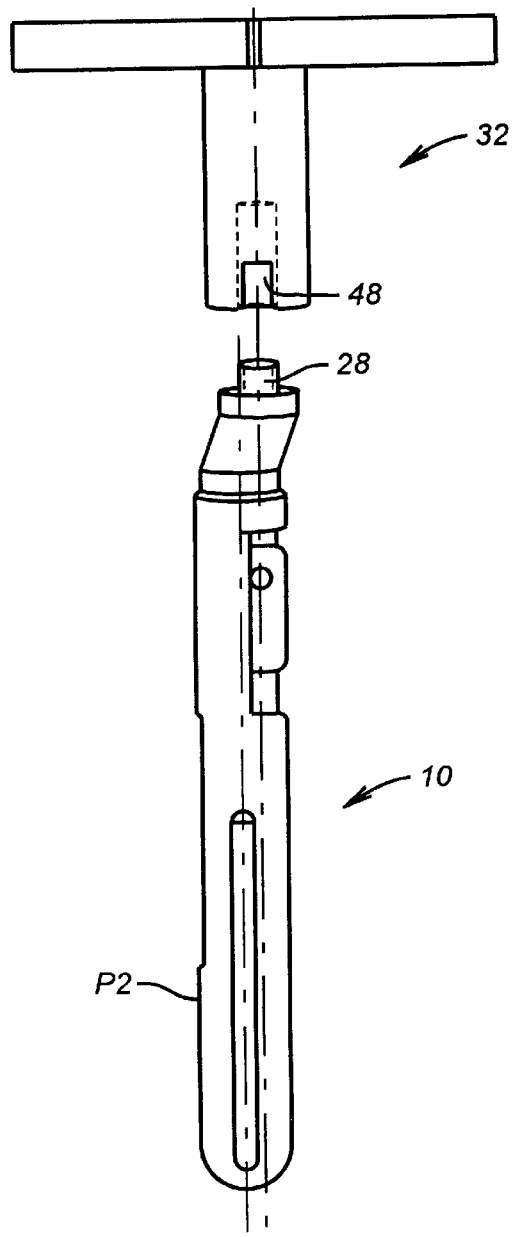
FIG. 5 is another frontal view illustrating the trial stem of FIG. 1 rotated 180 degrees.

A baseplate 32, FIGS. 2 and 3, includes a mounting portion 34 and a stem receiving recess 36 formed therein. Recess 36 is threaded to receive a threaded member, discussed below in greater detail. An end 36a of recess 36 includes a pair of keyed slots 46 and 48 adjacent thereto, see also FIG. 4, which are 180 degrees opposed to each other, for receiving tab 28. Thus tab 28 is inserted into either slot 46 or slot 48 to provide an offset in a first position P1, FIG. 1, e.g. a medial or lateral offset or in a second position, P2, 180 degrees opposite the first position, FIG. 5, e.g. a medial or lateral offset.

Figure 6:
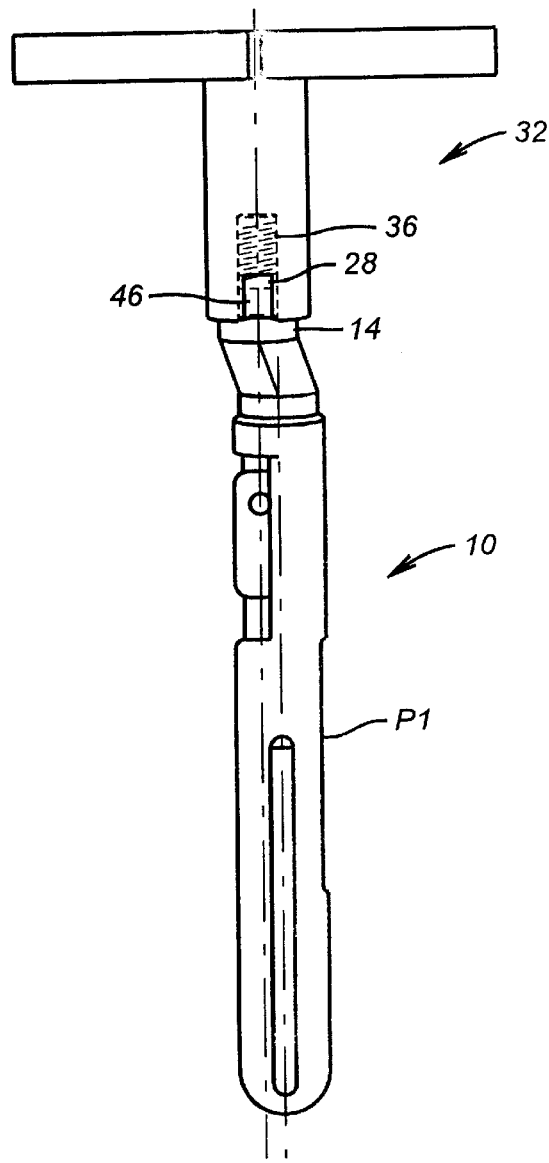
FIG. 6 is a frontal view illustrating trial stem of FIG. 1 engaged with the trial baseplate.

In FIG. 6, stem 10 is illustrated having baseplate connection portion 14 abutted with stem receiver portion 36. Tab 28 extends into slot 46 for a non-rotational connection between stem 10 and baseplate 32 in position P1. Stem 10 can be rotated 180 degrees to position P2, FIG. 5, so that tab 28 can be non-rotatably engaged with slot 48.

Stem 10, FIG. 4, includes a threaded member 50 attaching trial stem 10 to baseplate 32. Threaded member 50 is mounted for rotating and reciprocal movement in stem 10. Threaded member 50 seats in a blind bore 52 which extends through main body portion 12, transition portion 16, and baseplate connection portion 14. Bore 52 includes an open end 53 which opens at end surface 26 of baseplate connection portion 14. Member 50 includes an end 54 which normally seats in abutment with endwall 56 of blind bore 52. In this seated position, a threaded portion 58 of threaded member 50 is approximately flush with end surface 26 so as not to protrude through open end 53. An opening 60 formed in main body portion 12, exposes an enlarged diameter portion or thumb wheel 62 of threaded member 50, thus providing manual access to threaded member 50. Thumb wheel 62 limits reciprocal movement of threaded member 50 in a direction designated D1 toward open end 53, and endwall 56 of blind bore 52 limits reciprocal movement of threaded member 50 in a direction designated D2, opposite the direction designated D1. Bore 52 has a diameter generally greater than threaded member 50 and generally less than enlarged portion 62.

As a result of the forgoing construction, threaded member 50 may be manually reciprocated in the direction designated D1 so that threaded end 58 is extended out of open end 53 beyond end surface 26 Once extended, threaded member 50 may be manually rotated so that when baseplate connection portion 14 is abutted with mounting portion 34, threaded end 58 can be manually rotated into threaded engagement with threaded recess 36, thus connecting trial stem 10 to trial baseplate 32.

As it can be seen, the principal advantages of these embodiments are that the offset trial stem can be attached to the stem trial baseplate presently used with the straight trial stem. A reciprocating, rotatable threaded attachment combined with a tabbed clocking feature, positions the offset trial stem in the same orientation as that of an offset stem implant. The offset trial stem includes a thumb wheel incorporated into the main body portion of the trial stem without protruding beyond the outer diameter of the trial stem. To assemble the trial stem onto the trial baseplate, the trial stem is abutted up to the trial baseplate in the appropriate orientation so that the tab is inserted into the appropriate slot. An upward force combined with a rotation of the thumb wheel threads the trial stem into the trial baseplate. The surgeon is thus provided with a trial that will be the same fit as when the actual implant replaces the trial.

As a result, one embodiment provides an offset trial stem, including a main body portion, and a baseplate connection portion being offset from, and connected to, the main body portion by a transition portion. A threaded member is provided for attaching the trial stem to a baseplate. The threaded member is mounted for rotating movement in the trial stem.

Another embodiment provides an offset trial stem system including a baseplate and a trial stem. The trial stem has a main body portion and a baseplate connection portion. The baseplate connection portion is threadably attached to the baseplate, and is offset from, and connected to, the main body portion by a transition portion. A threaded member is provided for attaching the trial stem to the baseplate. The threaded member is mounted for rotating movement in the trial stem.

A further embodiment provides an offset trial stem system, including a baseplate and a trial stem. The baseplate has a stem receiving recess formed therein. The recess is keyed for receiving the trial stem in one of a first position and a second position. The trial stem has a main body portion and a baseplate connection portion. The baseplate connection portion is keyed to engage the stem receiving recess in one of the first position and the second position. A first means is provided for transitioning the baseplate connection portion to be offset from, and connected to, the main body portion. A second means is provided for threadably attaching the baseplate connection portion to the stem receiving recess. The second means is mounted for rotating movement in the trial stem.

A still further embodiment provides a method of mounting an offset trial stem system comprising the steps of forming a canal in a tibia by removing cancellous bone. A baseplate is attached to a trial stem having a baseplate connection portion offset from a main body portion by a transition portion. A threaded member is rotatably mounted in the main body portion for threaded attachment to the baseplate.

Although illustrative embodiments have been shown and described, a wide range of modifications, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. An offset trial stem comprising:
   a main body portion having an internal bore;
   a baseplate connection portion being offset from and connected to the main body portion, wherein the bore terminates in an opening at one end of the baseplate connection portion; and
   a threaded member being disposed within the bore and being rotatable in an axial direction and moveable in a longitudinal direction while in the bore.

2. The trial stem as defined in claim 1 wherein one end of the threaded member has external threads and protrudes from the opening at the one end of the baseplate connection portion.

3. The trial stem as defined in claim 1 in which the baseplate connection portion is integrally formed with the main body portion.

4. The trial stem as defined in claim 1 in which a first centroidal axis extends through the main body portion and a second centroidal axis extends through the baseplate connection portion, wherein the first and second centroidal axes are parallel, offset, and pass through the main body portion.

5. The trial stem as defined in claim 4 in which the offset is about 3 mm.

6. The trial stem as defined in claim 1 wherein the internal bore terminates in an endwall in the main body portion, and the threaded member is adapted to abut against the endwall.

7. The trial stem as defined in claim 1 wherein the threaded member has one end with external threads and a body having a thumb wheel with a diameter larger than a diameter of the one end with external threads.

8. The trial stem as defined in claim 7 wherein the main body portion includes an opening and the thumb wheel partially extends through the opening to limit movement of the threaded member in a longitudinal direction.

9. The trial stem as defined in claim 1 wherein the main body portion has a first centroidal axis passing therethrough, and the baseplate connection portion has a second centroidal axis passing therethrough, the offset being such that the first centroidal axis and the second centroidal axis each pass through the main body portion.

10. The trial stem as defined in claim 1 wherein the baseplate connection portion includes a tab that extends outwardly from the baseplate connection portion, the tab having a longitudinal axis that is parallel with a longitudinal axis of the bore.

11. The trial stem as defined in claim 10 wherein the threaded member has one end that protrudes from the opening at the one end of the baseplate connection portion, and the end of the threaded member extends parallel with and adjacent to the tab.

12. The trial stem as defined in claim 1 wherein the bore has an elongated cylindrical shape and extends completely through the baseplate connection portion and partially through the main body portion.

13. The trial stem as defined in claim 12 wherein the bore terminates at an endwall located within the main body portion.

14. The trial stem as defined in claim 13 wherein the threaded member extends from the endwall to the opening at the one end of the baseplate connection portion.

15. An offset trial stem system, comprising:
   a baseplate;
   a trial stem having a main body portion including a first opening and a baseplate connection portion including a second opening, the baseplate connection portion being threadably attached to the baseplate, and being offset from, and connected to, the main body portion by a transition portion; and
   a threaded member for attaching the trial stem to the baseplate, the threaded member being mounted for rotating movement in the trial stem and having a first portion in the first opening and a second portion in the second opening, whereby the first portion is movable reciprocally and rotatable to reciprocate and rotate the second portion.

16. The trial stem as defined in claim 15 wherein the threaded member is mounted for reciprocal movement in the stem.

17. The trial stem as defined in claim 16 wherein the threaded member is simultaneously rotatable in the stem and extendible from the stem.

18. The trial stem as defined in claim 16 wherein a first portion of the threaded member is rotatable in the stem and a second portion of the threaded member is extendible from the stem.

19. The trial stem as defined in claim 15 wherein the threaded member includes a first portion mounted in the main body portion of the stem and a second portion mounted in the baseplate connection portion of the stem.

20. The trial stem as defined in claim 15 wherein the threaded member is movable axially within the main body portion of the stem, the transition portion of the stem and the baseplate connection portion of the stem.

21. The trial stem as defined in claim 15 wherein the threaded member is mounted for reciprocal movement in the stem so that a threaded end thereof is extendible from the baseplate connection portion for attachment to the baseplate.

22. The trial stem as defined in claim 15 wherein the baseplate connection portion is keyed to mount with the baseplate in one of a first position and a second position, and the baseplate includes a stem receiving recess formed therein which is keyed for receiving the baseplate connection portion in one of the first position and the second position.

23. An offset trial stem system comprising:
   a baseplate, including a stem receiving recess formed therein, the recess being keyed for receiving a trial stem in one of a first position and a second position;
   the trial stem having a main body portion and a baseplate connection portion and an elongated cavity extending through the baseplate connection portion and into the main body portion;
   the baseplate connection portion being keyed to engage the stem receiving recess in one of the first position and the second position;
   first means for transitioning the baseplate connection portion to be offset from, and connected to, the main body portion; and
   second means for threadably attaching the baseplate connection portion to the stem receiving recess, the second means being mounted inside the cavity for rotating movement in the trial stem.

24. The trial stem as defined in claim 23 wherein the second means is mounted for reciprocal movement in the stem.

25. The trial stem as defined in claim 24 wherein the main body portion includes a first opening formed therein and the baseplate connection portion includes a second opening formed therein, the second means having a first portion in the first opening and a second portion in the second opening, whereby the first portion is movable reciprocally and rotatably to reciprocate and rotate the second portion into the stem receiving recess.

26. The trial stem as defined in claim 25 wherein the second means is simultaneously rotatable in the stem and extendible from the stem into the stem receiving recess.

27. The trial stem as defined in claim 24 wherein a first portion of the second means is rotatable in the stem and a second portion of the second means is extendible from the stem into the stem receiving recess.

28. The trial stem as defined in claim 23 wherein the second means includes a first portion mounted in the main body portion of the stem and a second portion mounted in the baseplate connection portion of the stem.

29. The trial stem as defined in claim 23 herein the second means extends axially within the main body portion of the stem, the transition portion of the stem and the baseplate connection portion of the stem.

30. The trial stem as defined in claim 23 herein the second means is mounted for reciprocal movement in the stem so that a threaded end thereof is extendible from the baseplate connection portion for attachment to the baseplate within the stem receiving recess.

31. A method of mounting an offset trial stem system, comprising the steps of:

forming a canal in a tibia by removing cancellous bone;

attaching a baseplate to a trial stem having a baseplate connection portion offset from a main body portion by a transition portion, wherein a bore extends through the baseplate connection portion and into the main body portion; and rotating a threaded member mounted inside the bore of the baseplate connection portion and main body portion to threadably attach to the baseplate.

32. The method of mounting an offset trial stem as defined in claim 31 wherein the step of rotating the threaded member further comprises the step of extending an end of the threaded member from the baseplate connection portion.

33. An offset trial stem connectable to a baseplate, the trial stem comprising:

a main body portion having a first centroidal axis;

a baseplate connection portion having a second centroidal axis and being offset from and connected to the main body portion, wherein first and second centroidal axes are parallel and pass through the main body portion; and a threaded member adapted to attach the main body portion and baseplate connection portion to a baseplate, the threaded member being mounted for rotating movement in the main body and baseplate connection portions.

34. An offset trial stem system comprising:

a baseplate, including a stem receiving recess formed therein, the recess being keyed for receiving a trial stem in one of a first position and a second position;

the trial stem having a main body portion with a first opening and a baseplate connection portion with a second opening;

the baseplate connection portion being keyed to engage the stem receiving recess in one of the first position and the second position;

first means for transitioning the baseplate connection portion to be offset from, and connected to, the main body portion; and second means for threadably attaching the baseplate connection portion to the stem receiving recess, the second means being mounted for rotating movement in the trial stem and having a first portion in the first opening and a second portion in the second opening, wherein the first portion is movable reciprocally and rotatably to reciprocate and rotate the second portion into the stem receiving recess.

* * * * *